US008759048B2

(12) United States Patent
Hagen

(10) Patent No.: US 8,759,048 B2
(45) Date of Patent: Jun. 24, 2014

(54) METHOD AND SYSTEM FOR COLLECTING ETHANOL FROM AQUATIC PLANTS

(75) Inventor: Tony A. Hagen, Sioux Falls, SD (US)

(73) Assignee: Aquatech Bioenergy LLC, Sioux Falls, SD (US)

( * ) Notice: Subject to any disclaimer, the term of this patent is extended or adjusted under 35 U.S.C. 154(b) by 615 days.

(21) Appl. No.: 12/940,491

(22) Filed: Nov. 5, 2010

(65) Prior Publication Data
US 2011/0086400 A1  Apr. 14, 2011

Related U.S. Application Data

(63) Continuation-in-part of application No. 12/730,213, filed on Mar. 23, 2010, now abandoned, which is a continuation-in-part of application No. 12/628,601, filed on Dec. 1, 2009, which is a continuation-in-part of application No. 12/437,333, filed on May 7, 2009, now Pat. No. 8,143,041.

(51) Int. Cl.
C12N 5/00 (2006.01)
C12N 5/02 (2006.01)
C12P 7/06 (2006.01)

(52) U.S. Cl.
USPC .......................................... 435/161; 435/410

(58) Field of Classification Search
None
See application file for complete search history.

(56) References Cited

U.S. PATENT DOCUMENTS

| 4,062,146 A | 12/1977 | Grossman et al. |
| 4,324,068 A | 4/1982 | Anthony |
| 4,532,210 A | 7/1985 | Miura et al. |
| 4,557,310 A | 12/1985 | Castellaw et al. |
| 6,395,521 B1 | 5/2002 | Miura |
| 7,135,308 B1 | 11/2006 | Bush et al. |
| 8,143,041 B2 | 3/2012 | Hagen |
| 2003/0024874 A1 | 2/2003 | Wallace |
| 2005/0061737 A1 | 3/2005 | Linden et al. |
| 2007/0062105 A1 | 3/2007 | Stevens |
| 2008/0153080 A1 | 6/2008 | Woods et al. |
| 2008/0176304 A1 | 7/2008 | Lee |
| 2010/0285551 A1 | 11/2010 | Hagen |
| 2010/0285554 A1 | 11/2010 | Hagen |
| 2011/0045561 A1 | 2/2011 | Hagen |
| 2011/0086401 A1 | 4/2011 | Hagen |
| 2011/0086419 A1 | 4/2011 | Hagen |
| 2013/0071902 A1 | 3/2013 | Hagen et al. |

FOREIGN PATENT DOCUMENTS

| EP | 0645456 A1 | 3/1995 |
| WO | WO2007101172 A2 | 9/2007 |
| WO | WO2008039450 A2 | 4/2008 |
| WO | WO2008047113 A2 | 4/2008 |

OTHER PUBLICATIONS

International Search Report issued in PCT/US2010/058174, mailed mailed Aug. 30, 2011, 14 pages.
Janssen, Marcel et al., "Scale-up aspects of photobioreactors: effects of mixing-induced light/dark cycles", Journal of Applied Phycology, 2000, vol. 12, pp. 225-237.
Miura, Y. et al., "Stimulation of hydrogen production in Algal Cells Grown Under High C(2 Concentration and Low Temperature", Applied Biochemistry and Biotechnology, copyright 1993, vol. 39/40, pp. 753-761.
Li, Y et al. "Oxygen enhances the recovery of Potamogeton maackianus from prolonged exposure to very low irradiance", Aquatic Botany 86 (2007) 295-299.
International Search Report issued in PCT/US2010/033335, mailed Dec. 17, 2010.
Summers, J.E., "Anoxia tolerance in the aquatic monocot Potamogeton pectinatus: absence of oxygen stimulates elongation in association with an usually large Pasteur effect," Journal of Experimental Botany, vol. 51, No. 349, pp. 1413-1422, Aug. 2000.
International Search Report and Written Opinion issued in PCT/2012/056261, dated Mar. 28, 2013, 11 pages.
European Search Report issued in EP Application No. 10772632, completed October 11, 2012, 8 pages.
Luo, Dexin et al., "Life Cycle Energy and Greenhouse Gas Emissions for an Ethanol Production Process Based on Blue-Green Algae", Environmental Science & Technology, vol. 44, No. 22, Nov. 2010, pp. 8670-8677, XP002684824, ISSN: 0013-936X.
Saygideger, Saadet Demirors et al., "Effect of 2, 4-dichlorophenoxyacetic acid on growth, protein and cholorphyll-a content of *Chlorella vulgaris* and *Spirulina platensis* cells", Journal of Environmental Biology, vol. 29, No. 2, Mar. 2008, pp. 175-178.
Summers, Jacky E. et al., "Anoxia tolerance in the aquatic monocot *Potamogeton pectinatus*: Absence of oxygen stimulates elongation in association with an unusually large Pasteur effect", Journal of Experimental Botany, vol. 51, No. 349, Aug. 2000, pp. 1413-1422.
Ueno, Yoshiyuki et al., "Ethanol Production by Dark Fermentation in the Marine Green Alga, *Chlorococcum littorale*", Journal of Fermentation and Bioengineering, vol. 86, No. 1, 38-43, 1998.
Written Opinion issued in PCT/US2010/033335, mailed Dec. 17, 2010, 4 pages.
Mishima, D. et al., Ethanol production from candidate energy crops: Water hyacinth (*Eichnornia crassipes*) and water lettuce (*Pistia stratiotes* L.) Bioresource Technology 99:2495-2500, 2007.

(Continued)

Primary Examiner — Debbie K Ware
(74) Attorney, Agent, or Firm — Faegre Baker Daniels LLP

(57) ABSTRACT

Methods and systems for collecting, purifying, and/or extracting ethanol produced during anaerobic metabolism by aquatic plants is provided. The system includes a cell containing water and an aquatic plant, an ethanol extraction assembly in fluid communication with the cell for removing ethanol from the water. Ethanol is released by the aquatic plant by initiating an anaerobic process in the plant such as by regulating the photosynthesis inducing light that reaches the aquatic plant.

10 Claims, 6 Drawing Sheets

(56) References Cited

OTHER PUBLICATIONS

Ailstock, M. Stephen "The Characterization of Axenic Culture Systems Suitable for Plant Propagation and Experimental Studies of the Submersed Aquatic Angiosperm *Potamogeton pectinatus*(Sago Pondweed)" vol. 14, No. 1, p. 57-64 Mar. 1991.

Anderson, Lars W.J., "A review of aquatic weed biology and management research conducted by the United States Department of Agriculture—Agricultural Research Service" Pest Manag Sci 59:801-813 (online: 2003) DOI: 10.1002/ps. 725.

Baldantoni, Daniela, "Analyses of three native aquatic plant species to assess spatial gradients of lake trace element contamination" Aquatic Botany 83 (2005) 48-60.

Colmer, T.D., "Root aeration in rice (*Oryza sativa*): evaluation of oxygen, carbon dioxide, and ethylene as possible regulators of root acclimatizations" New Phytologist (2006) 170: 767-778.

Colmer, Timothy, "Blackwell Publishing Ltd Underwater photosynthesis and respiration in leaves of submerged wetland plants: gas films improve $CO_2$ and O2 exchange" New Phytologist (2008) 177: 918-926.

Crump, Byron, "Attached Bacterial Populations Shared by Four Species of Aquatic Angiosperms" Applied and Environmental Microbiology, Oct. 2008, p. 5948-5957 vol. 74, No. 19.

Dixon, M.H., "Physiological and Metabolic Adaptations of *Potamogeton pectinatus* L. Tubers Support Rapid Elongation of Stem Tissue in the Absence of Oxygen" Plant Cell Physiol. 47(1): 128-140 (2006).

Ghobrial, M.G., "Influence of Barley Straw and Submerged Macrophytes on Fishpond Wastewater Quality" vol. 33 No. 3, 2007: 68-87.

Greger, Maria, et al., "A Tentative Model of Cd Uptake in *Potamogeton Pectinatus* in Relation to Salinity" vol. 35, No. 2, pp. 215 225, 1995.

Gruber, Renee., et al.,"Feedback effects in a coastal canopy-forming submersed plant bed" Limnol. Oceanogr., 55(6), 2010, 2285-2298.

Hangelbroek, Helen H. et al., "Local adaptation of the pondweed *Potamogeton pectinatus* to contrasting substrate types mediated by changes in propagule provisioning" Journal of Ecology 2003 91, 1081-1092.

Harada, Taro, et al., "Anoxia-enhanced expression of genes isolated by suppression subtractive hybridization from pondweed (*Potamogeton distinctus* A. Benn.) turions" Planta (2007) 226:1041-1052.

Harada, Taro, et al.. "Expression of Sucrose Synthase Genes Involved in Enhanced Elongation of Pondweed (*Potamogeton distinctus*) Turions under Anoxia" Annals of Botany 96: 683-692, 2005.

Harada, Taro, et al., "Starch Degradation and Sucrose Metabolism During Anaerobic Growth of Pondweed (*Potamogeton distinctus* A. Benn.) Turions" Plant and Soil 253: 125-135, 2003.

Hidding, Bert, et al., "How a Bottom-Dweller Beats the Canopy: Inhibition of an Aquatic Weed (*Potamogeton Pectinatus*) by Macroalgae (Chara spp.)", Freshwater Biology (2010) 55, 1758-1768.

Huang, Shaobai, et. al., "Manipulation of Ethanol Production in Anoxic Rice Coleoptiles by Exogenous Glucose Determines Rates of Ion Fluxes and Provides Estimates of Energy Requirements for Cell Maintenance During Anoxia," Journal of Experimental Botany, vol. 56, No. 419, pp. 2453-2463, Sep. 2005.

Ishizawa, K., "Growth and Energy Status of Arrowhead Tubers, Pondweed Turions and Rice Seedlings Under Anoxic Conditions," Plant, Cell and Environment (1999) 22, (505-514).

Jackson, Michael B., "Evolution and Mechanisms of Plant Tolerance to Flooding Stress," Annals of Botany 103: 137-142, 2009.

James, William F., "Effects of Lime-Induced Inorganic Carbon Reduction on the Growth of Three Aquatic Macrophyte Species," Aquatic Botany 88 (2008) 99-104.

Kennedy, Thomas L., "The Effects of Nitrate Loading on the Invasive Macrophyte *Hydrilla Verticillata* and Two Common, Native Macrophytes in Florida," Aquatic Botany 91 (2009) 253-256.

Koizumi, Yayoi, "Involvement of Plasma Membrane H+-Atpase in Anoxic Elongation of Stems in Pondweed (*Potamogeton Distinctus*) Turions," New Phytologist © 2011 New Phytologist Trust, doi: 10.1111/j.1469-8137.2010.03605.x, 10 pages.

Miller, Stephanie, A., "Mechanisms of Resistance of Freshwater Macrophytes to Herbivory by Invasive Juvenile Common Carp," Freshwater Biology (2007) 52, 39-49.

Ookawara, Ryuto, "Expression of a-Expansin and *Xyloglucan Endotransglucosylase*/Hydrolase Genes Associated with Shoot Elongation Enhanced by Anoxia, Ethylene and Carbon Dioxide in Arrowhead (*Sagittaria pygmaea* Miq.) Tubers," Annals of Botany 96: 693-702, 2005.

Rozentsvet, O.A., "Lipid Composition of *Potamogeton pectinatus* as a Function of Water Contamination," Chemistry of Natural Compounds, vol. 46, No. 5, 2010.

Sato, Tatsuhisa, "Stimulation of Glycolysis in Anaerobic Elongation of Pondweed (*Potamogeton distinctus*) Turions," Journal of Experimental Botany, vol. 53, No. 376, pp. 1847-1856, Sep. 2002.

Smart, R. Michael, "Techniques for Establishing Native Aquatic Plants," J. Aquat. Plant Manage. 36: 44-49 (1998).

Spencer, David F., "Competition between two submersed aquatic macrophytes, *Potamogeton pectinatus* and *Potamogeton gramineus*, across a light gradient," Aquatic Botany 92 (2010) 239-244.

Spencer, David F., "Construction costs for some aquatic plants," Aquatic Botany 56 (1997) 203-214.

Spencer, David F., "Dilute Acetic Acid Exposure Enhances Electrolyte Leakage by *Hydrilla Verticillata* and *Potamogeton Pectinatus* Tubers," J. Aquat. Plant Manage. 35: 25-30 (1997).

Spencer, David F., "Emergence of vegetative propagules of *Potamogeton nodosus*, *Potamogeton pectinatus*, *Vallisneria americana*, and *Hydrilla verticillata* based on accumulated degree-days," Aquatic Botany 67 (2000) 237-249.

Spencer, David F., "Influence of Propagule Size, Soil Fertility, and Photoperiod on Growth and Propagule Production by Three Species of Submersed Macrophytes," Wetlands, vol. 15, No. 2, Jun. 1995, pp. 134-140.

Spencer, David F. et al., "Soluble Sugar Concentrations Associated with Tuber and Winter Bud Sprouting", J. Aquat. Plant Manage. 39:45-47 (2001).

Summers, Jacky E., "Anaerobic promotion of stem extension in *Potamogeton pectinatus*. Roles for carbon dioxide, acidification and hormones," *Physrologia Plantarum* 96: 615-622. 1996.

Summers, Jacky E., "Light- and Dark-Grown *Potamogeton Pectinatus*, an Aquatic Macrophyte, Make No Ethylene (Ethene) But Retain Responsiveness to the Gas," Aust. J. Plant Physiol., 1998, 25, 599-608.

Sutton, David L., "Influence of Allelochemicals and Aqueous Plant Extracts on Growth of Duckweed," J. Aquat. Plant Manage. 27: 90-95 (1989).

Tamura, Shinsuke, "Involvement of Calcium Ion in the Stimulated Shoot Elongation head Tubers under Anaerobic Conditions," Plant Cell Physiol. 42(7): 717-722 (2001).

Tauskela, Joseph S., "A Regulated Environmental Perfusion System for the Study of Anoxic or Hypoxic Cultured Neurons Using Microfluorescence Imaging and Electrophysiology," pnugers Arch-Eur J Phys;ol (1998) 435: 775-780.

Van Den Berg, Marcel S., "Competition between Chara aspera and *Potamogeton pectinatus* as a function of temperature and light," Aquatic Botany 60 (1998) 241-250.

Voesenek, L.A.C.J., "The Role of Ethylene and Darkness in Accelerated Shoot Elongation of *Ammophila Breviligulata* Upon Sand Burial," Oecologia (1998) 115:359-365.

Winkel, Anders., "Use of Sediment CO2 by Submersed Rooted Plants," Annals of Botany 103: 1015-1023, 2009.

Woolf, Thomas E., "Seasonal Biomass and Carbohydrate Allocation Patterns in Southern Minnesota Curlyleaf Pondweed Populations," J. Aquat. Plant Manage. 41: 113-118 (2003).

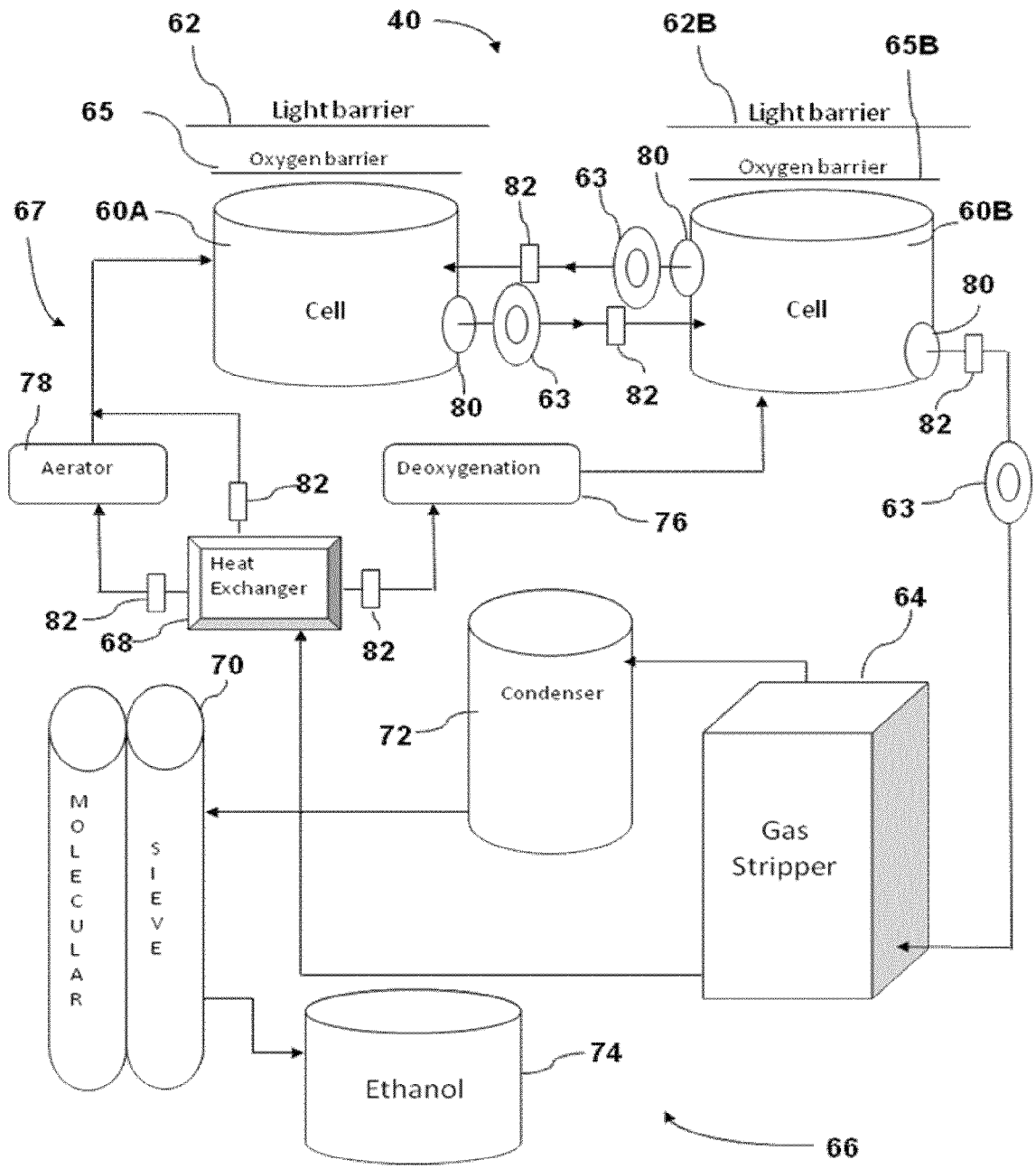

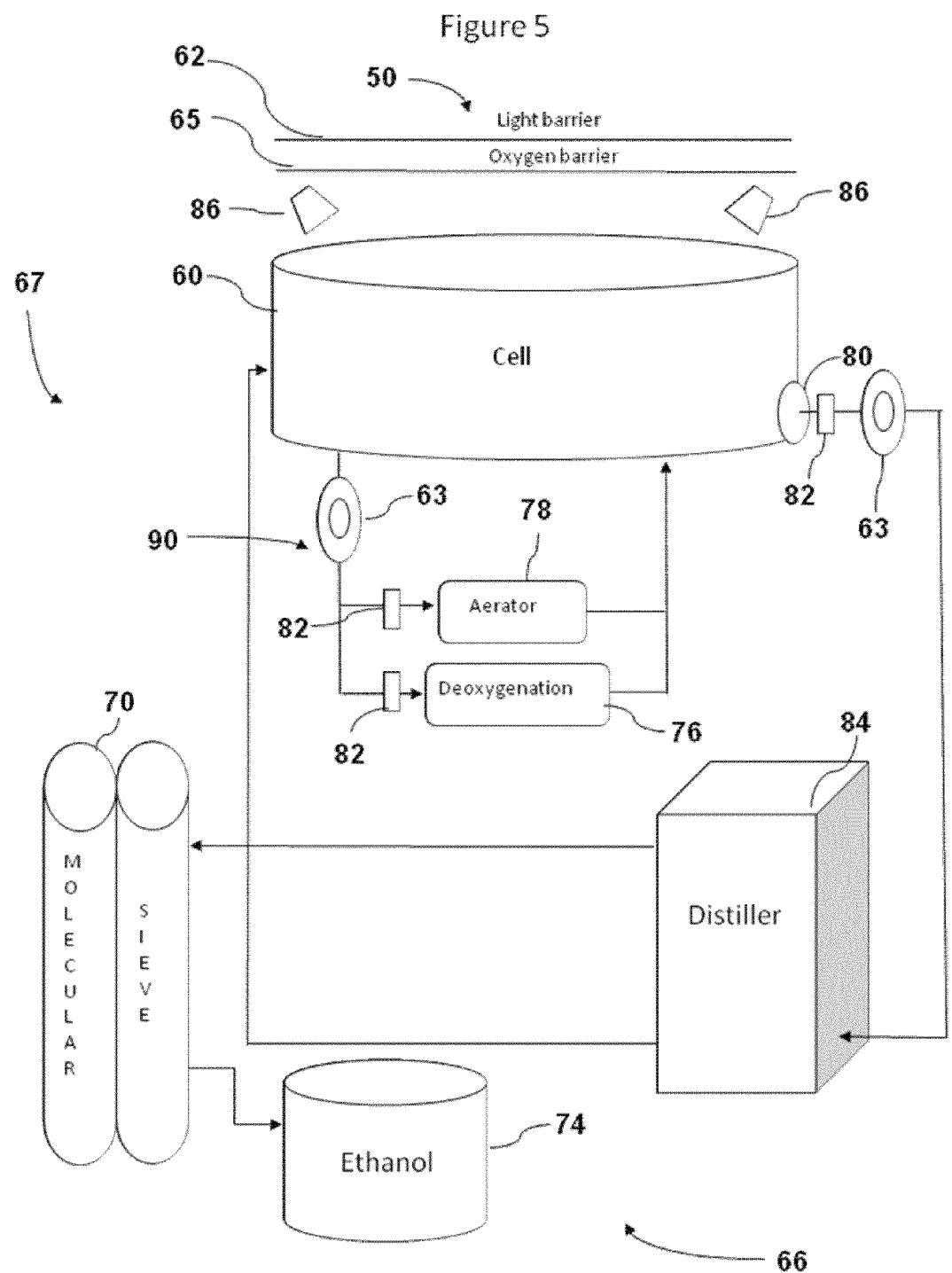

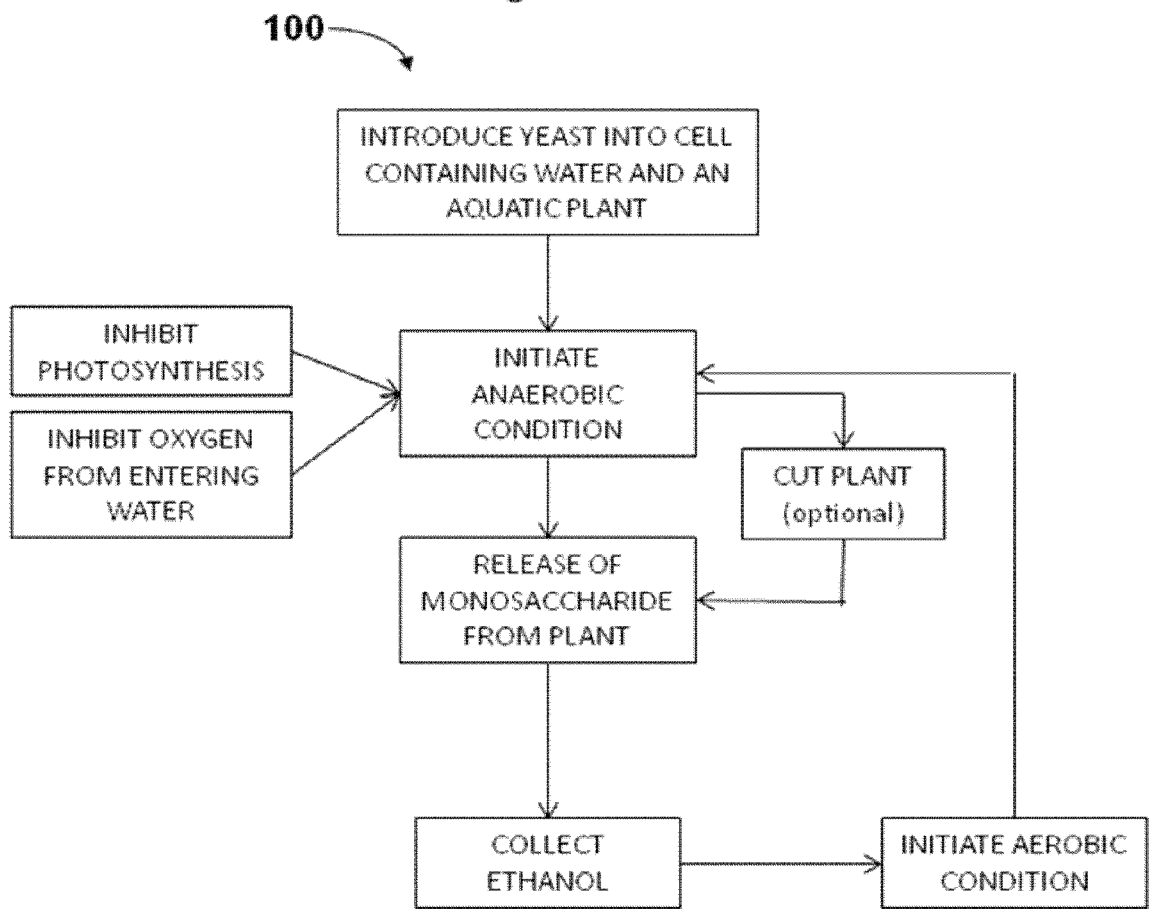

METHOD AND SYSTEM FOR COLLECTING ETHANOL FROM AQUATIC PLANTS

RELATED APPLICATIONS

This application is a continuation-in-part of U.S. patent application Ser. No. 12/730,213 filed May 23, 2010, which is a continuation-in-part of U.S. patent application Ser. No. 12/628,601 filed Dec. 1, 2009, which is a continuation-in-part of U.S. patent application Ser. No. 12/437,333 filed on May 7, 2009. Each of these applications is expressly incorporated by reference herein in its entirety.

BACKGROUND OF THE DISCLOSURE

Field of the Disclosure

The disclosure relates to ethanol production and collection systems and methods and more particularly pertains to a new ethanol production method for promoting plant growth by plants which produce free ethanol during anaerobic metabolism to form a self-sustaining cycle of plant growth and ethanol production. The disclosure also relates to a system for collecting, purifying, and/or extracting ethanol produced during anaerobic metabolism by aquatic plants.

SUMMARY OF THE DISCLOSURE

Provided herein are methods and systems for the collection, purification, and/or extraction of ethanol produced during anaerobic metabolism by an aquatic plant. The systems provided herein benefit from methods of ethanol production by an aquatic plant, including alternating steps of inducing aerobic and anaerobic metabolism in the plant.

One embodiment is an ethanol production and collection system, comprising a cell including water and at least one aquatic plant, and ethanol removal assembly in fluid communication with the water, and a photosynthetic light regulating system configured to inhibit photosynthesis in the aquatic plant.

Another embodiment is an ethanol production and collection system, comprising a cell including water and at least one aquatic plant, and ethanol removal assembly in fluid communication with the water, and a means for regulating photosynthesis inducing light allowed to reach the at least one aquatic plant. Exemplary means are disclosed herein.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawing wherein:

FIG. 4 is a schematic view of a system for isolating ethanol from aquatic plants according to an embodiment of the disclosure.

FIG. 5 is a schematic view of a system for isolating ethanol from aquatic plants according to an embodiment of the disclosure.

FIG. 6 is a schematic view of a method of obtaining ethanol from saccharides produced by aquatic plants according to an embodiment of the disclosure.

DETAILED DESCRIPTION

Figure 1:
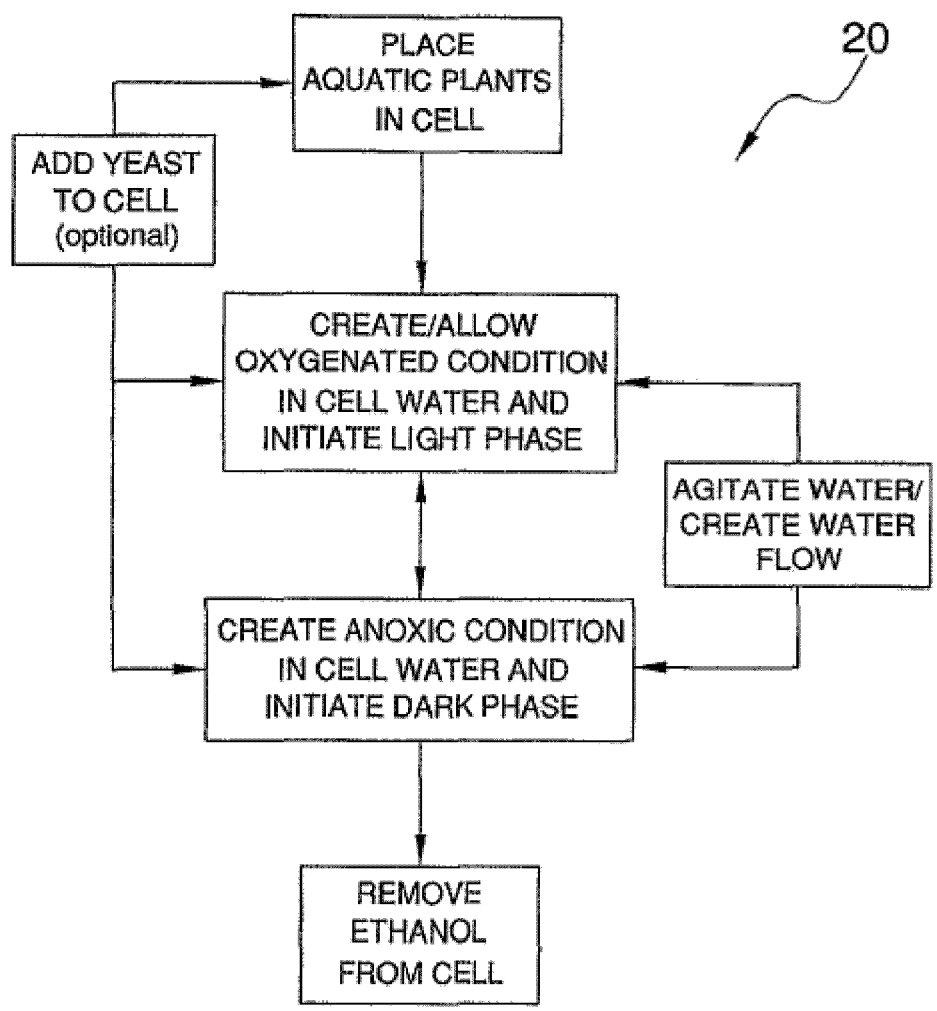
FIG. 1 is a schematic view of a method of stimulating ethanol production and growth of aquatic plants according to an embodiment of the disclosure.
Figure 2:
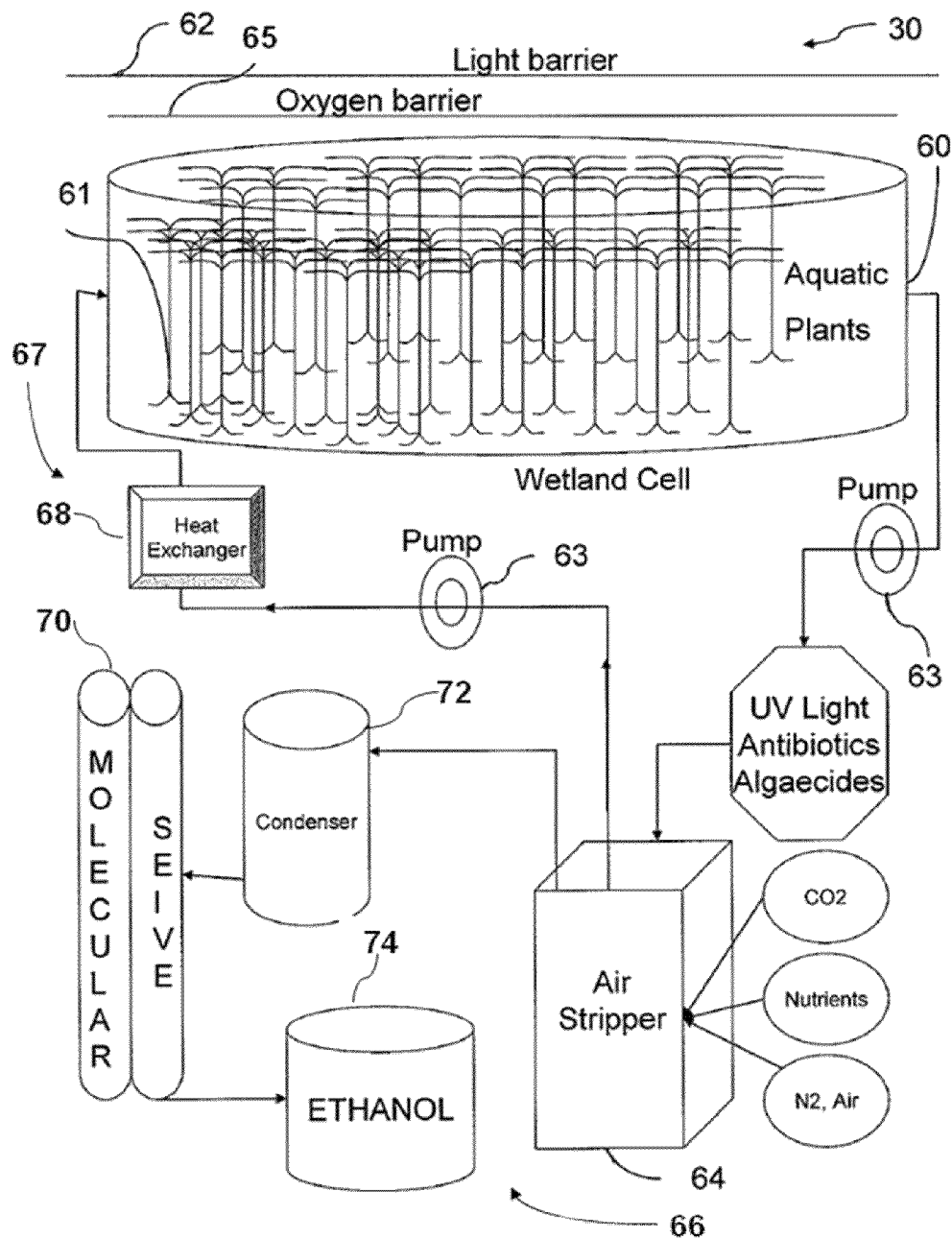
FIG. 2 is a schematic view of a system for isolating ethanol from aquatic plants according to an embodiment of the disclosure.
Figure 3:
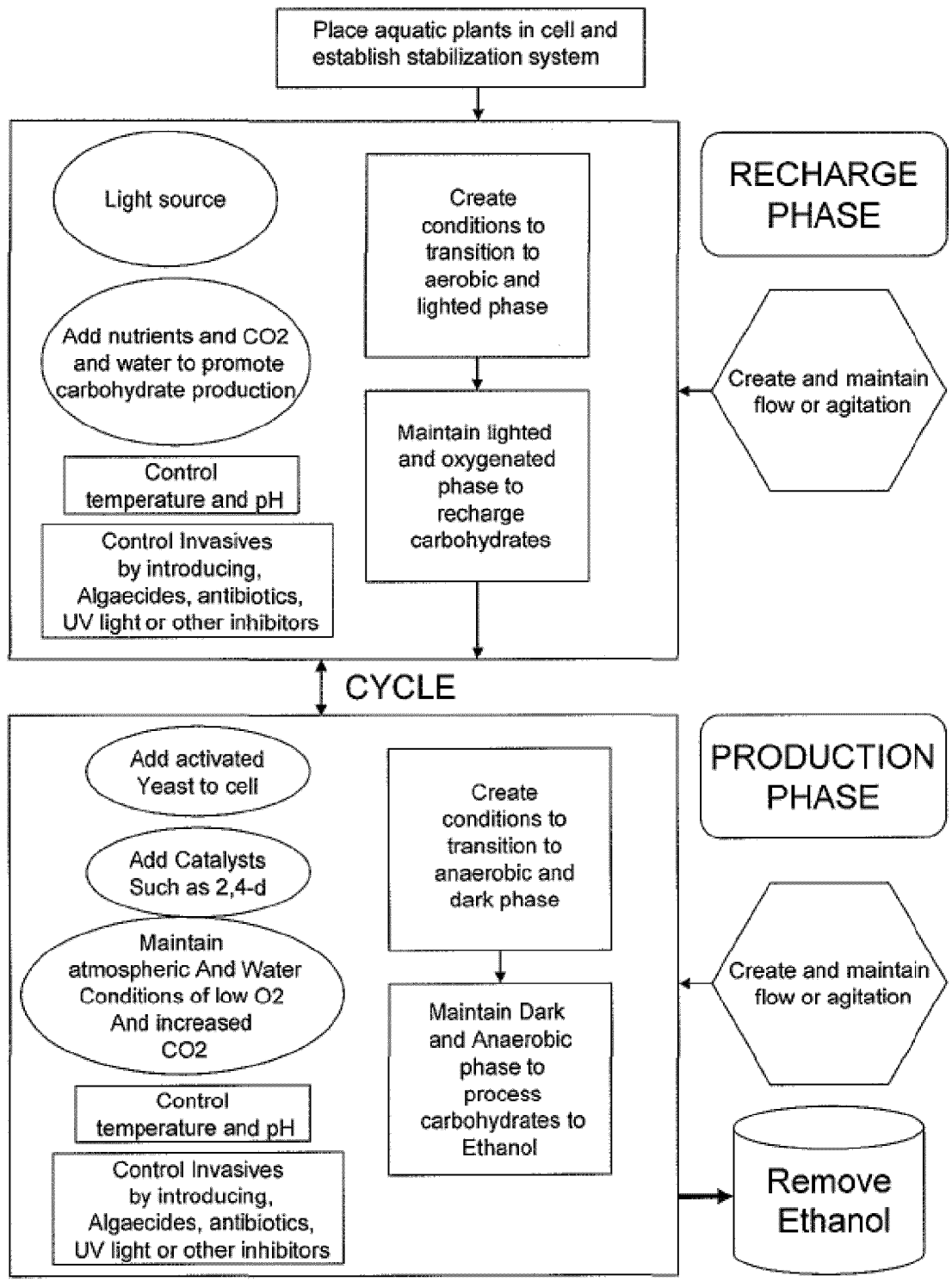
FIG. 3 is a schematic view of a method of stimulating ethanol production and growth of aquatic plants according to an embodiment of the disclosure.

With reference now to the drawings, and in particular to FIGS. 1 and 3, a new ethanol production method embodying the principles and concepts of an embodiment of the disclosure and generally designated by the reference numeral 20 will be described. FIG. 3 is a more detailed schematic view of FIG. 1. FIGS. 2, 4 and 5 illustrate various systems 30, 40, 50 based on the method 20.

As illustrated in FIGS. 1 and 3, the method 20 of stimulating ethanol production and growth of aquatic plants includes generally growing aquatic plants in one or more cells. Systems for the isolation of ethanol from an aquatic plant is provided herein based on the methods described below. The aquatic plants may be obtained and placed in the cell in any conventional manner such as gathering the plants from lakes or ponds, growing them in tanks or growing them directly in the cell. As the method 20 is performed, it may be used to grow and provide aquatic plants as they are needed for future cells or for replacement purposes. The type of water used in the cell will vary based on the plant type, but fresh water, salt water and brackish water are all suitable for various embodiments.

Each cell is constructed to hold water and may or may not be lined to prevent transfer of fluids and gases into a ground surface supporting the cell. The cells are dimensioned to hold one or more aquatic plants. The dimensions of cells will depend on the size and type of aquatic plant used, and on the depth required for the chosen aquatic plant to properly grow without restriction. The depth of each cell can range from about 10 cm to about 20 m (e.g., 10 cm to 100 cm, 50 cm to 1 m, 100 cm to 1 m, 500 cm to 3 m, 1 m to 5 m, 4 m to 10 m, 5 m to 7 m, 5 m to 10 m, or 10 m to 20 m). It has been found that some plants may grow in dramatically deeper depths providing other environmental factors, such as atypically high water temperatures at depth, are present. For instance, *Stuckenia pectinata* has been shown to grow in depths of greater than 20 m of water where thermal vents provide at least warmer water than would be typically found in a North American lake at such depths.

The width and length of a cell is not crucial to the system. It is to be understood that the cell width and length need not be equal, and can be adjusted to accommodate the number and type of plant to be used in the system, and can further depend on the cell shape, available land area, access to raw materials, and cost controls. When a cell is dimensioned to hold a single plant, it may be advantageous to include more than one cell in the system.

The cell may also be temperature controlled and in particular the cell should be prevented from freezing which may kill the aquatic plants. Heat for cells may be sequestered from waste heat emitted by adjacent ethanol processing plants or any other convenient source of waste heat. Additional heat sources, such as geothermic and solar, may also be utilized where convenient. In one embodiment, water exiting a waste water treatment plant or electricity facility may be utilized both to regulate temperature and to provide additional nutrients to the aquatic plants. Additionally, in particularly hot climates, the cells may require cooling to prevent temperatures that would otherwise harm the plants. Depending on the variety of aquatic plant being utilized, a temperature range may be selected which optimizes plant growth and ethanol production. For example, some selected plants such as *Stuckenia pectinata* may be maintained between 85° Fahrenheit and 73° Fahrenheit for optimal growth, though it should be understood that the overall temperature range for growth and production of ethanol falls into a much wider range. One manner of controlling temperature is to sink the cell into the ground where the soil around the cell will moderate the temperature of the cell.

A substrate, for example a fine particulate, may be placed in the cells and the aquatic plants introduced into the cells where they can anchor themselves in the particulate. A fine particulate may be used as it may promote less energy expenditure on the part of the aquatic plants to root growth into the particulate and retains a higher percentage of the plant matter above the surface of the particulate.

However, many of the plants being utilized by the method 20 primarily rely on their root systems as anchoring means and therefore any type of anchoring mechanism or substrate may be used which can be engaged by the roots. Additionally, a denser particulate may be useful where water flow within the cell requires a stouter anchoring substrate. Thus, a cell of a system provided herein may include mechanical anchoring devices, such as grids or screens, to which the roots may engage and couple themselves.

An aquatic plant may be selected from any number of aquatic plants which readily live in or on an aquatic environment such as directly in water or in permanently saturated soil. More generally, the term "aquatic plant" may include any algae, aquatic plant or semi-aquatic plant which has a high tolerance for either being constantly submerged in water or intermittently submerged during periods of flooding. Further, more than one type of aquatic plant may be used within a single cell.

The aquatic plants may include, for example, algae, submersed aquatic herbs such as, but not limited to, *Stuckenia pectinata* (formerly known as *Potamogeton pectinatus*), *Potamogeton crispus, Potamogeton distintcus, Potamogeton nodosus, Ruppia maitima, Myriophyllum spicatum, Hydrilla verticillate, Elodea densa, Hippuris vulgaris, Aponogeton boivinianus, Aponogeton rigidifolius, Aponogeton longiplumulosus, Didiplis diandra, Vesicularia dubyana, Hygrophilia augustifolia, Micranthemum umbrosum, Eichhornia azurea, Saururus cernuus, Cryptocoryne lingua, Hydrotriche hottoniiflora, Eustralis stellata, Vallisneria rubra, Hygrophila salicifolia, Cyperus helferi, Cryptocoryne petchii, Vallisneria americana, Vallisneria torta, Hydrotriche hottoniiflora, Crassula helmsii, Limnophila sessiliflora, Potamogeton perfoliatus, Rotala wallichii, Cryptocoryne becketii, Blyxa aubertii* and *Hygrophila difformmis*, duckweeds such as, but not limited to, *Spirodela polyrrhiza, Wolffia globosa, Lemna trisulca, Lemna gibba, Lemna minor,* and *Landoltia punctata,* water cabbage, such as but not limited to *Pistia stratiotes,* buttercups such as but not limited to Ranunculus, water caltrop such as but not limited to *Trapa natans* and *Trapa bicornis,* water lily such as *Nymphaea lotus,* Nymphaeaceae and Nelumbonaceae, water hyacinth such as but not limited to *Eichhornia crassipes, Bolbitis heudelotii,* and *Cabomba,* and seagrasses such as but not limited to *Heteranthera zosterifolia,* Posidoniaceae, Zosteraceae, Hydrocharitaceae, and Cymodoceaceae. Moreover, in one of the various embodiments, a host alga may be selected from the group consisting of green algae, red algae, brown algae, diatoms, marine algae, freshwater algae, unicellular algae, multicellular algae, seaweeds, cold-tolerant algal strains, heat-tolerant algal strains, ethanol-tolerant algal strains, and combinations thereof.

The aquatic plants in general may also be selected from one of the plant families which include Potamogetonaceae, Ceratophyllaceae, Haloragaceae, and Ruppiaceae. More particularly, the aquatic plants chosen should have a large Pasteur effect which increases the ratio of anaerobic $CO_2$ production to the aerobic $CO_2$ production. Typically this ratio is on the order of 1:3, but aquatic plants such as for example *Stuckenia pectinata,* formerly and also sometimes known as *Potamogeton pectinatus,* and commonly known as Sago Pondweed, may increase this ratio to 2:1 as explained in "Anoxia tolerance in the aquatic monocot *Potamogeton pectinatus*: absence of oxygen stimulates elongation in association with an usually large Pasteur effect," *Journal of Experimental Botany,* Volume 51, Number 349, pp. 1413-1422, August 2000, which is incorporated herein by reference. During an elongation process which takes place in a dark and anoxic environment, the plant elongates to form cellular chambers which will later be used to store carbohydrates formed during aerobic metabolism through an aerobic process of the aquatic plant. These carbohydrates can then be used to release ethanol during anaerobic metabolism through an anaerobic process of the aquatic plant. Generally, the equations are as follows:

Aerobic plant metabolism: 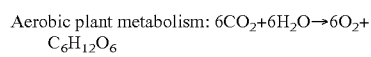

Anaerobic plant metabolism: 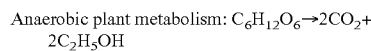

Once an aquatic plant is established in a cell, an anaerobic process is initiated in the aquatic plant, which facilitates the metabolism of stored carbohydrates into ethanol. In one embodiment the anaerobic process is initiated or facilitated by creating an anoxic condition (also referred to as anaerobic condition herein) in the cell. The term "anoxic" is here defined as a level of oxygen depletion that induces the plant to enter or maintain an anaerobic metabolic condition. Thus, an anoxic condition can be sufficient to reduce or maintain a level of intracellular oxygen in the plant to facilitate an anaerobic process or metabolism in the plant.

There are several approaches for creating an anoxic condition in the cell, and each approach may be used independently or in combination with one or more other approaches. In one embodiment, an anoxic condition is created by depleting or reducing a concentration of oxygen in the water contained in the cell. This may be accomplished by introducing water into the cell that is severely depleted (i.e. rendered anoxic) of oxygen through the use of organic, chemical, or mechanical means. This may also be accomplished by removing oxygen from water contained in the cell. It should be understood that the term "anoxic" does not necessarily indicate a complete absence of oxygen in the water, as a very small quantity of oxygen will likely be dissolved in the water.

This embodiment and other embodiments of the invention can be practiced with multiple cells wherein anoxic water and oxygenated water are rotated between the cells as needed to alternate between an anoxic condition and an oxygenated condition. For example, the process of utilizing multiple cells may include a first cell having anoxic water containing 2% ethanol, which is moved into a second cell having previously been oxygenated. The anoxic water replaces the removed oxygenated water in the second cell to create an anoxic condition in the second cell. Within the second cell plant growth and ethanol production are then stimulated. It is noted that having ethanol originally in the second cell (since the anoxic water contains ethanol from the anaerobic process of the first cell) may further spur ethanol production when the aquatic plants detect ethanol in the water. The ethanol concentration may be allowed to increase, for example, up to 4% in the second cell. Each time the anoxic water is moved into a new cell, the elongation and ethanol production of those plants is stimulated. Once the ethanol concentration of the anoxic water reaches a predetermined level, such as for example 10% by volume, the anoxic water is removed from the cell and the ethanol extracted from the water using conventional means.

Alternatively or additionally, oxygen reducing additives such as corn, yeast, bacteria (e.g., genetically altered bacteria and/or bacteria capable of fermentation), or enzymes, which consume oxygen and sugars while producing carbon dioxide, may be added to the cell to deplete the oxygen levels. In order to promote the depletion of oxygen levels, a secondary carbohydrate source, for instance corn, molasses, wheat or other sources of sugar, may be added to the water for use by the oxygen reducing additives. The secondary carbohydrate source may be added along with yeast to cause a strong enough reaction to remove a significant amount of oxygen from the system. One benefit of the reduction of oxygen may be additional production of ethanol by the oxygen reducing additives.

The lack of sufficient oxygen in the water facilitates the anaerobic process in the aquatic plants causing them to metabolize carbohydrates and to produce ethanol. The production of ethanol may be further encouraged by the introduction of chemical catalysts and $CO_2$. Suitable chemical catalysts include acetic acid and 2,4-dichlorophenoxyacetic acid (known generically as 2,4d). $CO_2$ may be obtained from waste sources such as electricity facilities and petroleum refineries. Additional nutrients and salts such as salts of potassium, nitrogen and phosphorus may further be added to promote growth of the aquatic plants. Further, depending upon the species of aquatic plant being utilized, organic substrates, including but not limited to those such as sucrose, glucose and acetate, may also be added to the cell.

During the anaerobic process, the aquatic plants can increase in size and may achieve a lengthening of up to 10 times or more of its original length. The term 'size' here is to be understood to include a volume increase of plant matter which allows for it to store a larger amount of carbohydrates. This elongation provides additional cellular chamber volume for holding carbohydrates to be later formed by the aquatic plants. Additionally during the anaerobic process, ethanol is produced intracellularly and released extra-cellularly by the aquatic plants. This ethanol is then held within the water of the cell until it is removed by methods further disclosed below.

This anaerobic process may take place from one to several days. In the case of *Potamogeton pectinatus* (or *Stuckenia pectinata*) a total of six days may suffice, though longer periods, such as up to 14 days may be more beneficial to maximize output efficiencies. The time required will depend on many factors such as light diffusion, availability of nutrients, size of the cell, size of the plant, plant variety and carbon content of the plant. The plant may be allowed to stay in anoxic conditions for up to several weeks. The determination of length of time is primarily dependent upon maximizing output of ethanol. When the plant decreases its ethanol production beyond useful parameters, there may be no need to retain it in the anoxic conditions. Further, the pH of the cell must be monitored to prevent the water from becoming too acidic or basic. This may be counteracted with calcium buffering compounds such as calcium carbonate and calcium chlorate or by introducing $CO_2$ (to basic water), but will ultimately be dependent upon the tolerances of the particular aquatic plant species in the cell.

In another embodiment, the anaerobic process may be initiated and/or facilitated by regulating the amount of photosynthesis inducing light that is allowed to reach the plant. In particular, during the anaerobic period, the cell may be shielded from light sources which encourage photosynthesis. This lack of light encourages the anaerobic process and the release of ethanol and prevents the formation of oxygen through photosynthesis. The light may be regulated by any conventional method to create dark conditions within the cell. It should be understood that the term "light" which should be blocked only applies to those forms of radiation, or wavelengths of light, which act as a photosynthesis catalyst and is dependent upon the type of chemical receptors used by each plant. Therefore, the term "dark" as used herein is meant to denote the substantial absence of the frequencies of light which promote photosynthesis.

Various means for regulating (e.g., selectively blocking/allowing) photosynthesis inducing light to reach the aquatic plant may be utilized. Such means include, for instance, barriers, covers, domes or other enclosure structure, which serve as a light barrier at least during the anaerobic process. These aforementioned barriers, covers, etc., may be removable when it is no longer desired to maintain the aquatic plant in an anaerobic condition. In one embodiment, the cells are illuminated by light visible to humans but which facilitates the "dark" condition for the plant. Other suitable regulation means include light filters that diffuse photosynthesis inducing light. Artificial lights sources may be used to preserve the dark condition and/or to selectively allow photosynthesis when the anaerobic condition is not desired.

In further embodiments, the anaerobic process may be facilitated by covering the cells with one or more sealing barriers to regulate the movement of gasses (e.g., air, oxygen, $CO_2$, nitrogen, etc.) into and out of the cell. For example, a sealing barrier may prevent the unwanted introduction of oxygen into the cell. The sealing barrier (or an additional sealing barrier) may also be used to retain $CO_2$ within the cell, particularly if $CO_2$ is being added to the cell. Additionally, high $N_2$ levels may be maintained as well to further dilute any $O_2$ within the water or trapped between the seal and the cell. The sealing barrier would seal the cell to prevent fluid communication between the cell and the adjacent atmosphere. This will inhibit oxygen from entering the cell and will encourage the anaerobic process. The sealing barrier may be a translucent barrier to encourage the capturing of radiant heat from a light source which is either naturally and/or artificially used to provide light to the aquatic plants. The sealing barrier may or may not also constitute a light blocking barrier which, as discussed above, is positioned on the cell to prevent light from entering the cell during the anaerobic process. The sealing and light blocking barriers may be made of conventional materials. However, it should be understood that a dwelling, tank, dome or other structure constructed around the cell may also define sealing and light block barriers should they be used in such a capacity.

In one embodiment, the anaerobic process described above is preceded by, followed by or alternated with an aerobic process. The aerobic process is initiated and/or facilitated in the aquatic plant by creating an oxygenated condition in the cell, which facilitates the production and storage of carbohydrates by the aquatic plant. This oxygenated condition may be created by a variety of approaches, which may be used independently or in combination. In one embodiment, oxygenated water is added to the cell or oxygen is directly introduced into water contained in the cell. In another embodiment, the gas barrier is removed to allow the oxygen concentration of the water to naturally increase. Accordingly, the oxygenated condition may be accomplished by introducing oxygenated water into the cell, by removing anoxic water and/or allowing the water to oxygenate naturally by plant releasing of oxygen and exposure to an oxygenated atmosphere.

In a further embodiment, which may be used independently or in combination with other embodiments, the aquatic plant is exposed to light to induce photosynthesis and to stop the anaerobic process by allowing an oxygenated condition within the cell, which initiates and/or facilitates the aerobic process. This "light condition" may be accomplished by manipulating the light regulating means and systems discussed herein. For example, a light barrier, cover, or filter etc., may be removed so that natural or artificial photosynthesis inducing light is allowed to reach the aquatic plant. Alternatively or additionally, a light barrier may remain in place and an artificial light source is regulated to allow photosynthesis inducing light to reach the aquatic plant.

During the aerobic process, waste materials, such as waste biomass from the method 10, industrial waste, municipal waste and the like may be added to the cell to provide nutrients to the aquatic plants. Additionally, maximum sunlight/artificial light filtration is encouraged as is temperature regulation to promote growth of the aquatic plants. The light itself may be intensified by the addition of artificial light.

Generally, the light phase is continued for between ½ day and 15 days, and more generally at least 3 to 6 days, to allow the aquatic plants to form sugars, though this time frame may be adjusted for plant specific requirements. During the aerobic process, as indicated above, the aquatic plants create carbohydrates through metabolic processes and then retain the carbohydrates within their elongated structures. The duration of the aerobic process is dependent upon a number of factors but will typically end when carbohydrate production begins to slow or reaches a predetermined level. With *Potamogeton pectinatus* (*Stuckenia pectinata*) this may be between 2 days and 14 days depending upon environmental conditions within the cell.

It has been found in particular that manipulating light and dark conditions can affect the manner in which the aquatic plants produce ethanol and sugars. For instance, some aquatic plants may be subjected to light for several continuous days defining a light phase followed by restriction to light for several continuous days defining a dark phase to facilitate the anaerobic, ethanol producing, process. In one embodiment, a dark condition is timed to occur simultaneously or shortly before or after the initiation of an anaerobic condition, preferably within 3 days of one another. One plant, *Stuckenia pectinata*, has been shown to have a light phase for up to about 6 days after which its production of sugars levels off or reaches a predetermined optimal level. The term "day" is defined as 24 hours. This plant has a dark phase of between about 2 days and 30 days during which it may enter the anaerobic process and produce ethanol. Generally, the ratio of light phase to dark phase will be no more than 1:2 and as small as 1:10, with a more common ratio of between 1:2 and 1:7. It should be understood that during both of the light and dark phases, $CO_2$ may be added to the water to encourage both the formation of sugar and ethanol. Finally, the ability to control the light and dark phases above and the ratios described herein are not applicable to all aquatic plants as certain plants may experience ethanol production after less than 4 hours of dark phase. For these types of aquatic plants, the ratio of light phase to dark phase may be greater than 2:1, though such aquatic plants may have different limitations with respect to ethanol production than experienced with plants such as *Stuckenia pectinata*.

Once maximum carbohydrate formation, or a predetermined level of such, is approached an anaerobic process is again initiated to begin the process of carbohydrate metabolism and ethanol formation. Although the process set forth above commences with an anaerobic phase followed by an aerobic phase, it will be appreciated that either phase can be initiated first after establishing the aquatic plant in the cell. The steps of creating anoxic conditions and oxygenated conditions can be repeated to continually promote elongation and ethanol production followed by carbohydrate production. This creates a self-sustaining cycle as the plant growth replenishes both plant matter lost to plant senescence and those plants which no longer meet established tolerances of ethanol production. Additional plant growth which cannot be used for replenishing purposes or for furnishing plant material for another cell may be removed and fermented using conventional methods to also produce ethanol. Carbon dioxide released during the fermentation process may be captured and returned to the cell to promote carbohydrate production. Plant waste, both before or after the fermentation process, may further be used for replenishing nutrients to the cell as feed material and/or may be processed for biochemical industrial usage such as in ethanol and diesel biofuels, pharmaceuticals, cosmetics, colorants, paints and the like. When the light phase ends, there may be a transition period between the oxygenated phase and the anoxic phase where the amount of oxygen is being depleted. During the transition period, it may be beneficial to add the yeast to the cell which will stimulate the reduction of the oxygen and will allow the yeast to produce the ethanol. The ethanol formed by the yeast may act as a catalyst for anaerobic activity by the plant and will offer an additional ethanol production outlet. Sugars or other carbohydrates added along with the yeast may further enhance anaerobic activity.

This three part cycle may more broadly be defined to include: 1) a recharge phase wherein the water is oxygenated and/or the plant is exposed to light so that carbohydrates are formed, 2) a transition phase wherein the water is being made anoxic, the cell is deprived of photosynthesis inducing light and/or yeast may be added to form ethanol and deplete oxygen, and 3) an anoxic phase wherein the plant enters an anaerobic process of releasing ethanol. A fourth phase may be defined as a second transition phase wherein the water is again allowed to become oxygenated. The phases may each be modified as taught herein to maximize plant growth and ethanol output. In one method, the recharge phase may occur over 0.5-12 days, followed by 0.5-6 days of the transition phase, which is then followed by at least 6 days of anoxic phase which may be increased to more than 20 days depending on the type of plant being utilized. In another method, the recharge phase may occur over 3-6 days, followed by 2-6 days of the transition phase, which is then followed by at least 6 days of anoxic phase which may be increased to more than 20 days depending on the type of plant being utilized.

Additional steps may be taken to increase plant growth and to further stimulate the production of ethanol. For instance, in order to increase ethanol formation and to prevent stagnation of the water, and eventual killing of the aquatic plants, the water can be continually agitated using a water agitation system to encourage the movement of water around and through the aquatic plants. This prevents the buildup of ethanol and other plant waste materials adjacent to the plant and brings nutrients to the plant. It has been further found that agitation of the water promotes the suspension of water additives such as yeast. An agitation system may include any form of wave movement through the plants or a sustained flow of water through the plants. Such a water movement system may be fluidly coupled to a circulation loop which removes the ethanol from the water after the water is piped or otherwise directed from the cell and before the water is returned to the cell. In some embodiments, while water is outside the cell in such a system, nutrients, antibiotics, $O_2$, $CO_2$, yeast, or any other required or desired additives may be added to the water. Additionally, a circulation loop may be used to also remove the $O_2$ from the water to make the water anoxic before it is returned to the cell to create the anoxic condition.

It has also been found that controlling the life cycles of the aquatic plants may be beneficial in lengthening the life spans of the aquatic plants. In particular, the life of some of the aquatic plants terminates after the flowering of those plants. This can be prevented by the cutting off of a top portion of the aquatic plants before they can flower. Such cutting will stop some of the aquatic plants from reaching the surface of the water and flowering. The plants may also be systemically cut and partially harvested to remove dead plant material and to thin the cell to allow for adequate light diffusion into the cell. The material cut may be allowed to remain in the cell to replenish nutrients to the cell.

While the method 20 is being practiced, bacterial and algal blooms may occur which can be controlled by antibiotics, bi-sulfates, hops, algaecides, chlorination, ultraviolet light exposure and other common practices. However, it has been discovered that that method 20 produces free carbohydrates, and in particular monosaccharides, which encourage bacterial growth within the cell. For this reason, it has been found to be beneficial to introduce ethanol producing yeasts into the cell for the purpose of decreasing the carbohydrate concentrations and inhibiting bacterial growth. Alternatively, or in conjunction with yeast, enzymes or bacteria may also be used to decrease carbohydrate concentrations. A beneficial outcome of the addition of yeast is an increase in ethanol output. As with the anaerobic process, the general equation for this process is $C_6H_{12}O_6 \rightarrow 2CO_2+2C_2H_5OH$ and is well known in the arts. The yeast may require replacement, particularly after the anoxic condition has been established and maintained for more than about three days, though this is dependent upon the strain of yeast being used. A secondary carbohydrate source may also be added to the system to cause the yeast to react more strongly.

FIG. 6 depicts method 100 for collecting ethanol from yeast. The method 100 is based generally on method 20 and may be carried out using the systems 30, 40 and 50 described herein. Method 100 generally includes the steps of establishing an aquatic plant in a cell, introducing yeast into the cell, initiating an anaerobic condition to encourage the production of free carbohydrates (e.g., monosaccharides) by the plant, allowing the yeast to convert free carbohydrates into ethanol, and collecting the ethanol. This method 100 can be used as the sole means for producing and collecting ethanol, or it can be used in conjunction with other processes described herein for producing and collecting ethanol.

The anaerobic condition can be initiated in method 100 in any of the approaches discussed herein, including by inhibiting photosynthesis-inducing light from reaching the plant or by inhibiting oxygen from entering the water. In some embodiments, the anaerobic condition is initiated by both inhibiting photosynthesis-inducing light from reaching the plant and inhibiting oxygen from entering the water. The introduction of yeast into the cell can be done at one or more time points during the method 100.

In embodiments of the method 100 which rely primarily or entirely on yeast conversion of carbohydrates to ethanol, the plant can be cut or damaged to further encourage the release of carbohydrates by the plant. In some embodiments, the plant can be cut or damaged along a stalk or a leaf. In other embodiments, the plant can be cut at the roots. A plant can be cut or damaged using any appropriate method. For example, an aquatic plant can be cut using an underwater cutter similar to those used for underwater weed management. In some embodiments, the plant can be broken or damaged, without cutting, to encourage the release of carbohydrates. For example, an aquatic plant can be broken or damaged using a rake.

In some embodiments, the method 100 includes initiating an aerobic condition to facilitate the storage of carbohydrates in the plant. An aerobic condition can be initiated in method 100 at any appropriate time point using the methods and systems described herein. For example, an aerobic condition can be initiated when the free carbohydrates have been depleted, when yeast ethanol production becomes inefficient, or when the ethanol concentration reaches a predetermined level. The point at which an aerobic condition is initiated can depend on various conditions, such as yeast strain (e.g., ethanol tolerance or fermentation efficiency), plant type (e.g., ethanol tolerance, carbohydrate storage efficiency), equipment used for ethanol collection, and the like.

After an aerobic period, an anaerobic condition can be reinitiated by, for example exposing the cell to natural or artificial light. In some embodiments, the aquatic plant and/or yeast can be replaced as necessary after an aerobic period. In some embodiments, the yeast in method 100 can be replaced by fermenting bacteria.

FIGS. 2, 4, and 5 depict systems 30, 40, and 50, respectively, for carrying out the described methods. It is to be understood that components and aspects from each of the depicted systems 30, 40, 50 can be combined, added, removed, or rearranged as appropriate to perform the method 20 described.

FIG. 2 depicts one system 30 particularly well suited for use with a single cell, though it should be understood that this system may also be used with multiple cells. This system 30 generally includes a cell 60 containing water and at least one aquatic plant 61, and an ethanol removal assembly 66 in fluid communication with the cell 60. The cell 60 may be sunken into the ground surface or in a dwelling foundation, a partially sunken tank structure or a fully above ground tank structure. The cell 60 may have any particular shape, though a circular or loop type cell may be beneficial for encouraging the movement of water within the cell 60. The water may be moved in a conventional manner though one utilizing a gravity lift system may prove to be beneficial due to its lower power requirements. The system 30 further includes one or more sealing barriers 65, which inhibit the movement of gasses such as oxygen and/or $CO_2$ into and out of the cell.

A photosynthetic light regulating system 62 is utilized to selectively allow/inhibit photosynthetic inducing light into the cell. A number of light regulation means are discussed with respect to the method 20, any of which may constitute all or a part of the light regulating system 62. For example, the light regulating system 62 can include a light-blocking cover or barrier over one or more cells 60. Alternatively or additionally, the light regulating system 62 includes a structure in which the cell 60 is housed or contained. It is to be understood that the light regulating system 62 can, but is not required to, inhibit all light from reaching a plant of the system. Rather the light regulating system 62 may only inhibit light at a wavelength or intensity that would induce photosynthesis in a plant of the system. For example, the light regulating system 62 can be a filter that allows only wavelengths that do not induce photosynthesis to pass. Examples of wavelengths that induce photosynthesis include wavelengths from about 380 nm to about 710 nm. Depending on the plant being used in the system 30, the range of wavelengths that induce photosynthesis can be broader or narrower, but can be ascertained using known methods. In one embodiment, the sealing barrier 65 and the light regulating system 62 constitute a single structure that may or may not be separable.

The light regulating system 62 can be configured to be adjustable to allow photosynthesis-inducing light at some time points, such as during aerobic metabolism or to induce aerobic metabolism, while inhibiting photosynthesis-inducing light at other time points, such as during anaerobic metabolism or to induce anaerobic metabolism. For example, the light regulating system 62 can be removable. In another example, the light regulating system 62 can be electrochromic, such that opacity or color of the apparatus can be controlled by the application of electric current. In some embodiments, the light regulating system 62 can include an artificial light source 86 such as shown in FIG. 5 to provide photosynthesis-inducing light and/or light that does not induce photosynthesis. Such an artificial light source 86 can be configured to emit light at an intensity or spectrum appropriate for the desired condition. For example, an artificial light source 86 can emit light at low intensity or having a wavelength outside of the range of photosynthesis-inducing light for a plant of the system during a period of anaerobic metabolism or to induce anaerobic metabolism. Similarly, artificial lighting can emit light at an intensity or at a wavelength for photosynthesis induction during aerobic metabolism of a plant of the system or to induce aerobic metabolism.

A heat source such as a heat exchanger 68 may be used to obtain an optimal temperature for the particular aquatic plant 61 or plants being used. Other suitable heat sources include conventional water heaters, geothermal energy sources, solar energy sources and waste heat from conventional electrical and petroleum facilities. Water may be pulled out from and reintroduced into the cell by pumps 63 through a closed loop system 67 to provide fluid communication between the cell 60 and the ethanol removal assembly. The closed loop system 67 may include an access point to the water to allow all additives discussed above to be supplied to the water without over exposing the water to the atmosphere. Alternatively, the cell 60 may include an access point.

The ethanol removal assembly 66 may include a variety systems and system components that are capable of extracting and collecting ethanol from the water. In the illustrated embodiment, the assembly 66 includes one or more air strippers (also known as gas strippers) 64 that function to separate ethanol from water. The gas stripper 64 (e.g., atmospheric air-, $N_2$-, or $CO_2$-based gas stripper) is in fluid communication with one or more of a condenser 72 for capturing ethanol vapor, a molecular sieve 70 for purifying the vapor, and/or a container 74 to store the ethanol. A pervaporator (not shown) could also be used if desired. The assembly 66 allows the ethanol to be removed continuously without interrupting the anaerobic and aerobic processes being carried out in the cell. The gas stripper 64 may be further utilized to allow for the introduction of $CO_2$, nitrogen, and nutrients into the water as well. Prior to introducing water back into the cell 60, it may be exposed to ultraviolet light and/or antibiotics and algaecides may be added to maintain a healthy cell 60 free of unwanted bacterial and algae growths. In some embodiments, the ethanol storage container 74 is replaced with an assembly for distributing the ethanol for use or transportation (not shown).

FIG. 4 depicts a system 40 that is similar in overall structure and function as system 30, but includes two or more cells 60A, 60B, some or all of which are directly or indirectly connected in fluid communication with one another. The cells 60A, 60B can be connected by any appropriate means. In some embodiments, two or more cells are connected by a common permeable wall. In another embodiment, two or more cells are connected by fluid conduits. The connection can be severable. For example, two or more cells can be connected by a pipe that includes a closable valve 82 to disrupt fluid communication between the two or more cells 60A, 60B. In some embodiments one cell 60A or 60B serves as a source of oxygenated water or anoxic water for the other cell 60A or 60B via the fluid conduits.

In some embodiments, a closed loop system 67 similar to that used in system 30 can be implemented to provide fluid communication between the ethanol removal assembly 66 and the cells 60A, 60B. As shown, cells 60A, 60B and ethanol removal assembly 66 are connected such that water from cell 60B is delivered to the ethanol removal assembly 66, and the water remaining after extracting the ethanol is returned to cell 60A. In an alternate embodiment, each of cells 60A and 60B may be independently in fluid communication with the ethanol removal assembly 66.

Additional components shown in FIG. 4 that may be used in system 30, 40 or 50 include an aerator 78, an oxygen removal apparatus 76 (e.g., a vacuum pump) and/or one or more filters 80 for removing particulate matter, such as plant material, substrate, and microorganisms (e.g., yeast or bacteria). The ethanol removal assembly 66 shown in FIG. 4 may function similarly to the assembly described with respect to FIG. 2.

FIG. 5 depicts system 50 that includes a closed loop system 67 between cell 60 and ethanol removal assembly 66 that is similar to the closed loop system 67 illustrated in FIG. 2. The system further includes a circulation loop 90 having an aerator 78 and/or an oxygen removal apparatus 76 to treat water moved through the circulation loop 90 by pump 63. In some embodiments, the oxygen removal apparatus 76 is replaced by a source of anoxic water (not shown) and/or the aerator 78 is replaced by a source of oxygenated water. A circulation loop 90 can be configured for the introduction of additives or to include components for the removal of oxygen from water. In some embodiments, a valve 82 is included in the circulation loop 90 to adjust the flow rate and direction of water in the circulation loop 90. The circulation loop 90 may also function to agitate the water in the cell, or a separate water agitator may be contained in the cell. As previously described with respect to system 30, system 50 includes an artificial light source 86 that serves as a light regulating system 62 alone or in conjunction with light barriers, etc. In particular, artificial light source 86 may provide photosynthesis-inducing light during a light period and/or non-photosynthesis-inducing light during a dark period.

The ethanol removal assembly of system 50 differs from those illustrated in FIGS. 2 and 4 in that a distiller 84 (e.g. a distillation column) is utilized instead of an gas stripper. A distiller and/or an gas stripper could be utilized in any of the illustrated systems. For example, an gas stripper 64 can be included in a system at a point where the concentration of ethanol is relatively low, while a distiller 84 can be included in a system at a point where the concentration of ethanol is higher. An ethanol removal assembly can be included in any point of a system and in any combination appropriate to remove ethanol from water in the system. In some embodiments, an ethanol removal assembly is included at multiple points in a system.

In a further embodiment, the ethanol removal assembly of any of the illustrated systems can use one or more ethanol absorptive collection systems alone or in combination with any of the other components disclosed herein. Generally speaking, ethanol absorptive collection systems utilize membrane or other absorption technology to separate ethanol from water and other extraneous materials. An example of such a membrane is the "Siftek" membrane manufactured by Vaperma Gas Separation Solutions.

The systems 30, 40, 50 can be integrated or associated with various other systems. For example, the systems 30, 40, 50 can be configured to sequester waste heat emitted by adjacent ethanol processing plants or any other convenient source of waste heat. In another example, the systems 30, 40, 50 are associated with a wastewater treatment plant, which typically has a constant source of water at a stable temperature of about 50° Fahrenheit to about 85° Fahrenheit. Waste water from electrical facilities may also be utilized. When associated with a wastewater source, water in a cell 60 can be regulated by heat exchange from the wastewater, or wastewater can be used directly in the cell 60 before or after initial wastewater treatment. In addition to providing a water source with a higher temperature, wastewater sources may also have nutrient concentrations that are favorable to plant growth.

It will be evident that the various components of systems 30, 40, 50 described herein can be used in various combinations to carry out the method 20. Additionally, conventional components can be included for controlling water flow, removing particulates, monitoring and/or maintaining water parameters (e.g., pH), monitoring ethanol concentration, monitoring and/or maintaining plant parameters, cutting, damaging or removing plants, and the like. For example, a system 30 provided herein can include components such as valves 82, filters 80, light sensors and/or meters (e.g., photosynthetically active radiation sensor), pH meters, and the like.

EXAMPLES

Example 1

Ethanol Production in Aquatic Plants

Two *Stuckenia pectinata* plants with tubers attached were removed from stock growth tanks and individually placed into a test tube with 35 ml of boiled distilled water. A Resazurin indicator was included in the water to show anoxic conditions. These anoxic samples were placed within foil wraps to produce dark conditions by preventing photosynthesis-inducing light from reaching the plants, which would allow the water within the plant cells to become re-oxygenated. The samples were then placed in a chamber with a positive pressure nitrogen atmosphere to prevent re-oxygenation of the extra-cellular sample water. The samples were then allowed to incubate in this chamber at 76 degrees Fahrenheit for 3 days. On the morning of the fourth day a 2 ml sample of water was removed from each sample and analyzed by high pressure liquid chromatography (HPLC) at South Dakota State University to detect the presence of ethanol. HPLC peaks in each sample indicated that ethanol was present.

Example 2

The Effect of Light and Antibiotics on Ethanol Production in Aquatic Plants

*Stuckenia pectinata* plant samples were taken from lake material gathered from South Dakota lakes and were placed in vials with boiled distilled water to provide anoxic conditions added only to cover plants. Eight samples, D5-8, D11, and D14-16 were placed in a sealed stainless steel pot within the incubator to provide dark conditions for the samples. The remaining samples, D1-4, D9-10, and D12-D13, were placed in clear plastic quart containers with airlocks. Antibiotic was added to samples D9-D16 to prevent ethanol conversion to acetic acid by bacteria. The samples were placed in an incubator at approximately 69 degrees Fahrenheit and allowed to incubate for 7 days. Water from each sample was drawn and analyzed by high pressure liquid chromatography (HPLC) at South Dakota State University to determine ethanol and acetic acid concentrations.

The four samples, D5, D6, D7, and D8, incubated without antibiotic in dark conditions contained ethanol at a concentration of 10.825 g/L, 6.817 g/L, 7.733 g/L, and 10.595 g/L, respectively. Samples D11 and D 14, which were incubated in dark conditions with antibiotic had ethanol concentrations of 6.573 g/L and 4.237 g/L, respectively. In addition, sample D11 contained no acetic acid, while sample D14 contained acetic acid at a concentration of 2.192 g/L, suggesting that the amount of antibiotic in sample 14 was insufficient to prevent ethanol conversion to acetic acid by bacteria. The samples incubated in the clear containers contained no detectable ethanol, suggesting that photosynthesis interfered with ethanol production by the plant samples. The results are shown in Table 1.

TABLE 1

| Sample | Dark conditions | Antibiotic | Acetic acid (g/L) | Ethanol (g/L) |
|---|---|---|---|---|
| D1 | − | − | 1.332 | 0 |
| D2 | − | − | 1.616 | 0 |
| D3 | − | − | 0.503 | 0 |
| D4 | − | − | 1.142 | 0 |
| D5 | + | − | 2.204 | 10.825 |
| D6 | + | − | 2.865 | 6.817 |
| D7 | + | − | 1.420 | 7.733 |
| D8 | + | − | 5.091 | 10.595 |
| D9 | − | + | 0 | 0 |
| D10 | − | + | 0 | 0 |
| D11 | + | + | 0 | 6.573 |
| D12 | − | + | 0.863 | 0 |
| D13 | − | + | 0.749 | 0 |
| D14 | + | + | 2.192 | 4.237 |
| D15 | + | + | 0.730 | 0 |
| D16 | + | + | 0 | 0 |

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

What is claimed is:

1. A method for generating ethanol from an aquatic plant, the method comprising:
   establishing at least one submersed aquatic herb in a cell containing water;
   alternating a step of inhibiting photosynthesis inducing light from reaching said at least one submersed aquatic herb to initiate and maintain an anaerobic metabolism in said at least one submersed aquatic herb and a step of allowing photosynthesis inducing light to reach said at least one submersed aquatic herb to initiate and maintain aerobic metabolism in said at least one aquatic herb; and
   generating ethanol from the aquatic plant.

2. The method of claim 1, further including a step of depleting oxygen in said water during the step of inhibiting photosynthesis inducing light from reaching said at least one submersed aquatic herb.

3. The method of claim 1, wherein a photosynthetic light inhibiting apparatus positioned between a light source and said at least one submersed aquatic herb inhibits photosynthesis inducing light from reaching said at least one submersed aquatic herb.

4. The method of claim 1, wherein a sealing barrier positioned between an oxygen source and said at least one submersed aquatic herb inhibits oxygen from entering said water.

5. The method of claim 1, wherein an artificial light source is positioned between the cell and a photosynthetic light regulating system.

6. The method of claim 1, further including the step of introducing anoxic water to said cell.

7. The method of claim 1, further comprising adding $CO_2$ to the water contained in said cell.

8. The method of claim 1, wherein the submersed aquatic herb is selected from a member of the group consisting of Potamogetonaceae, Ceratophyllaceae, Haloragaceae, or Ruppiaceae family.

9. The method of claim 8, wherein the submersed aquatic herb is from the Potamogetonaceae family and is *Stuckenia pectinata*.

10. The method of claim 1, further comprising collecting the ethanol from water contained in said cell.

* * * * *